US012686705B2

(12) United States Patent
Baumann et al.

(10) Patent No.: US 12,686,705 B2
(45) Date of Patent: Jul. 21, 2026

(54) BACTERIAL EFFECTOR AS ANTI-BACTERIAL PROTEIN

(71) Applicant: BATTELLE MEMORIAL INSTITUTE, Columbus, OH (US)

(72) Inventors: Heather Baumann, Charlottesville, VA (US); Rachael Hardison, Powell, OH (US); Fadime Kara Murdoch, Upper Arlington, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 486 days.

(21) Appl. No.: 18/331,686

(22) Filed: Jun. 8, 2023

(65) Prior Publication Data

US 2023/0399365 A1      Dec. 14, 2023

Related U.S. Application Data

(60) Provisional application No. 63/351,078, filed on Jun. 10, 2022.

(51) Int. Cl.
| | |
|---|---|
| *A61P 31/04* | (2006.01) |
| *A61P 31/14* | (2006.01) |
| *C07K 14/195* | (2006.01) |
| *A61K 38/00* | (2006.01) |
| *A61K 48/00* | (2006.01) |

(52) U.S. Cl.
CPC ............ *C07K 14/195* (2013.01); *A61P 31/04* (2018.01); *A61P 31/14* (2018.01); *A61K 38/00* (2013.01); *A61K 48/00* (2013.01)

(58) Field of Classification Search
CPC ................................ C07K 14/196; A61P 31/04
See application file for complete search history.

(56) References Cited

U.S. PATENT DOCUMENTS

2006/0051380 A1      3/2006      Schulick et al.

FOREIGN PATENT DOCUMENTS

WO            2005/049642 A2      6/2005

OTHER PUBLICATIONS

Ngwaga et al., "Potentiation of Cytokine-Mediated Restriction of Legionella Intracellular Replication by a Dot/Icm-Translocated Effector." J Bacteriol. 2019, vol. 201(14): e00755-18. PDF File: p. 1-14.
PCT Search Report and Written Opinion for International Application No. PCT/US23/68111, mailed Jan. 4, 2024.
Shames et al., "Multiple Legionella pneumophila effector virulence phenotypes revealed through high-throughput analysis of targeted mutant libraries." Proc Natl Acad Sci USA, 2017, vol. 114(48), p. E10446-E10454.
Weber et al., "Legionella pneumophilia Exploits PI(4)P to Anchor Secreted Effector Proteins to the Replicative Vacuole." PLoS Pathog. 2006, vol. 2(5): e46. p. 0418-0430.
Partial Supplementary European Search Report for Application No. 23820640.3, dated Nov. 11, 2025, 27 pages.
Database UniProt EMBL, Chien M. et al., Coiled-coil-containing protein, Jan. 19, 2022, 2 pages.
Shames, et al., Supporting Information, SI Materials and Methods, vol. 114, No. 48, Nov. 13, 2017, 8 pages.
Extended European Search Report for Application No. 23820640.3, dated Feb. 2, 2026, 25 pages.
Shames, et al., Multiple Legionella pneumophila effector virulence phenotypes revealed through high-throughput analysis of targeted mutant libraries, Proceedings of the National Academy of Sciences, National Academy of Sciences, vol. 114, No. 48, Nov. 28, 2017, 8 pages.
Tshegofatso, et al., Potentiation of Cytokine-Mediated Restriction of Legionella Intracellular Replication by a Dot/Icm-Translocated Effector, Journal of Bacteriology, American Society for Microbiology, US, vol. 201, No. 14, Jun. 30, 2019.

*Primary Examiner* — Amber D Steele

(74) *Attorney, Agent, or Firm* — Barnes & Thornburg

(57) ABSTRACT

Disclosed are methods of using the *Legionella pneumophilia* effector protein, LegC4, either intracellularly generated or extracellularly delivered to cells, as an anti-microbial agent to treat or prevent intracellular microbial infections.

19 Claims, 3 Drawing Sheets
Specification includes a Sequence Listing.

|  | 24 h | 48 h | 72 h | 96 h |
|---|---|---|---|---|
| LegC4-GFP | | | | |
| LegC4 | | | | |
| Untransfected | | | | |

BACTERIAL EFFECTOR AS ANTI-BACTERIAL PROTEIN

CROSS-REFERENCE TO RELATED APPLICATIONS

This application claims priority to U.S. Provisional Patent Application No. 63/351,078 filed on Jun. 10, 2023, the disclosure of which is hereby expressly incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 6 kilobytes xml file named "390720.xml" created on May 25, 2023.

BACKGROUND

*Legionella pneumophila* is ubiquitous in freshwater environments, where it replicates within unicellular protozoa. However, *L. pneumophila* is also an opportunistic human pathogen that can cause Legionnaires' disease in immuno-compromised individuals by uncontrolled replication within alveolar macrophages. To replicate within eukaryotic phago-cytes, *L. pneumophila* utilizes a Dot/Icm type IV secretion system to translocate a large arsenal of over 300 effector proteins directly into host cells. In mammals, translocated effectors contribute to innate immune restriction of *L. pneumophila.*

Innate immunity in healthy individuals effectively controls *Legionella* infection due in part to rapid and robust production of proinflammatory cytokines resulting from detection of Dot/Icm-translocated substrates, including effectors. More specifically, it has been reported that the effector LegC4 is important for *L. pneumophila* replication within a natural host protist but is deleterious to replication in a mouse model of Legionnaires' disease. LegC4 has been found to enhance restriction of *L. pneumophila* replication within macrophages activated with tumor necrosis factor (TNF) or interferon gamma (IFN-v). In addition, expression of legC4 was sufficient to restrict *Legionella longbeachae* replication within TNF- or IFN-γ-activated macrophages. Thus, LegC4 contributes to *L. pneumophila* clearance from healthy hosts by potentiating cytokine-mediated host defense mechanisms.

There exists a need for alternative or supplemental treatment for microbial pathogens besides antibiotics, which are losing their effectiveness due to pathogen resistance. As disclosed herein the use of bacterial effector proteins represents a promising alternative or supplemental treatment for combatting microbial pathogens.

SUMMARY

As pathogens acquire antibiotic resistance, currently available antimicrobial treatments are waning in effectiveness to treat bacterial diseases. Within the population of current therapeutics that remain effective, there is an even smaller subset that effectively targets and treats intracellular pathogens. The present disclosure is directed to the use of bacterial effector proteins to potentiate cytokine-mediated host defense mechanisms and limit the ability of intracellu-lar pathogens to infect and/or replicate in mammalian cells, including human cells. The bacterial effector proteins can be introduced into mammalian cells using any of the known standard techniques of introducing nucleic acids that encode the effector proteins into cells or introducing the effector proteins themselves into cells.

In one embodiment the bacterial effector protein used in accordance with the present disclosure is the LegC4 effector protein of *L. pneumophila.* LegC4 that is intracellularly-produced or extracellularly-delivered represents a novel therapeutic to strengthen the ability of the host to resist infection and/or interfere with pathogen replication or viability. Since this approach does not target essential processes in pathogens, unlike antibiotics, the use of LegC4 (or other bacterial effector proteins) has the potential to be a long-term antimicrobial agent without the risk of antibiotic resistance. A long-term therapeutic agent not susceptible to pathogen resistance has a significant economic benefit. Intracellular pathogenic infections are more challenging to treat and have higher rates of relapse, and therefore, a therapeutic that enhances the host's ability to clear intrac-ellular pathogens will have a cost savings since repeat treatments will not be needed. Additionally, this approach will not contribute to the progression of antibacterial resis-tance when used as a therapeutic against bacterial pathogens, including but not limited to intracellular bacterial pathogens.

In accordance with one embodiment a method of treating or preventing an intracellular pathogen infection in a mam-malian cell is provided, wherein the method comprises introducing a LegC4 polypeptide or a fragment thereof into the mammalian cell. In accordance with one embodiment a method of treating mammalian cells to inhibit the replication and/or reduce the numbers of an intracellular pathogen present in mammalian cells is provided. In one embodiment the method of treating or preventing an intracellular patho-gen infection in a mammalian cell comprises the step of increasing the intracellular concentration of a polypeptide having 95% sequence to SEQ ID NO: 2 (LegC4) in said cells, with the proviso that the intracellular bacterial patho-gen is not *Legionella pneumophilia.* In one embodiment the intracellular concentration of a polypeptide having at least 95% sequence to SEQ ID NO: 2 is increased by transfecting said cells with a polynucleotide that encodes said polypep-tide.

BRIEF DESCRIPTION OF THE DRAWINGS

FIG. 1A presents a graph showing the survival of *Salmonella* over time. FIG. 1B presents a graph showing the log reduction of *Salmonella* in transfected cells vs untransfected cells. **, $p<0.005$, *, $p<0.05$ by ANOVA.

DETAILED DESCRIPTION

Definitions

Figure 1A:
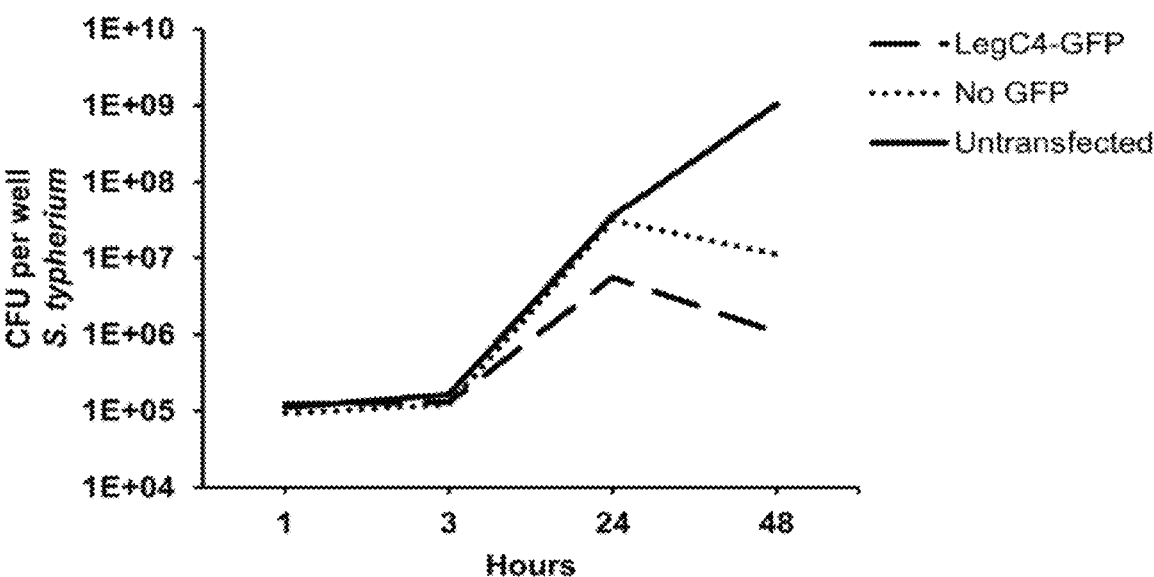
FIGS. 1A-1B: Intracellular Survival of *Salmonella* in LegC4 Infected Cells.

"Cell" refers to the basic structural and functional unit of a living organism. In higher organisms, e.g., animals, cells having similar structure and function generally aggregate into "tissues" that perform particular functions. Thus, a tissue includes a collection of similar cells and surrounding intercellular substances, e.g., epithelial tissue, connective tissue, muscle, nerve.

"Co-administration" refers to administration of unit dosages of two or more bioactive agents, wherein the active agents are administered simultaneously, or sequentially within a timeframe where the first administered agent is still therapeutically active when the last co-administered agent is administered.

"Effective amount" is that amount sufficient, at dosages and for periods of time necessary, to achieve a desired therapeutic result, such as for treatment of a disease (e.g. cancer) or condition, and/or achieve a pharmacokinetic or pharmacodynamic effect of the treatment in a subject. A therapeutically effective amount can be administered in one or more administrations. The therapeutically effective amount may vary according to factors such as the disease state, age, sex, and weight of the subject.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Subject" refers to any mammal for whom diagnosis, treatment, or therapy is desired including mammals, e.g., humans, laboratory animals (e.g., primates, rats, mice, rabbits and guinea pigs), livestock (e.g., cows, sheep, goats, and pigs), household pets (e.g., dogs, cats, and rodents), and horses.

"Treat," "treating" or "treatment" refer to an action to obtain a beneficial or desired clinical result including, but not limited to, alleviation or amelioration of one or more signs or symptoms of a disease or condition (e.g., regression, partial or complete), diminishing the extent of disease or condition, stability (i.e., not worsening, achieving stable disease) of the state of disease or condition, amelioration or palliation of the disease state or condition, diminishing rate of or time to progression, and remission (whether partial or total). For example, treating an intracellular pathogen includes decreasing the ability of the pathogen to infect, replicate or maintain viability in a host cell.

As used herein the term "an intracellular pathogen inhibitor" defines any agent or condition that has a detrimental effect on an intracellular pathogen's viability or its ability to infect or replicate either as a direct causative agent or by inducing production of an agent or condition unfavorable to the pathogen. Thus, as used herein an inhibitor can act directly or indirectly and either as a stand-alone treatment or in conjunction with another active moiety or condition. Inhibiting an intracellular pathogen defines the process of reducing the intracellular pathogen's viability or its ability to infect or replicate either directly or by inducing the production of an intracellular pathogen inhibitor.

As used herein a "microbial pathogen" is any microorganism that is capable of producing disease, including bacteria, fungal, viral, protist organisms.

An "intracellular pathogen" is an organism that is capable of growing and reproducing inside host cells. These pathogens can be divided into facultative intracellular pathogens and obligate intracellular pathogens, with facultative intracellular pathogens being capable of growing and reproducing both inside and outside host cells.

An "anti-microbial agent" is any compound or condition that has an adverse effect on a microbial organism's ability to grow, replication or infect host cells.

A "bacterial effector" as used herein defines a protein secreted by pathogenic bacteria that help the pathogen to invade host tissue, suppress its immune system, or otherwise help the pathogen to survive.

As used herein, the term "heterologous" in reference to a nucleic acid describes a nucleic acid sequence that originates from a foreign species or, if from the same species, represents a recombinant construct comprising a first heterologous nucleic acid sequence linked to a second nucleic acid sequence. For example a "heterologous" promotor is a promoter that has been operably linked to a coding sequence, by deliberate human intervention, to form a recombinant chimeric gene, wherein the promoter and coding sequence are not associated with each other in nature.

EMBODIMENTS

The present disclosure is directed to compositions and methods of using bacterial effector proteins to potentiate cytokine-mediated host defense mechanisms and limit the ability of intracellular pathogens to infect and/or replicate in mammalian cells, including human cells. The method can be used to treat and/or prevent an infection by pathogens selected from fungi, bacteria, and viruses but excluding the bacterial pathogen *Legionella pneumophilia*.

The therapeutic bacterial effector proteins of the present disclosure can be introduced into mammalian cells using any of the known standard techniques of introducing nucleic acids and polypeptides into cells. Introducing or increasing the concentration of a bacterial effector protein in a host cell can be conducted either by introducing an exogenous source of the polypeptide into the cell or by expressing a nucleic acid sequence in the cell that encodes the bacterial effector protein. In one embodiment nucleic acid sequences encoding the effector proteins or polypeptide fragments thereof are introduced into cells. Alternatively, the effector polypeptide itself, or a polypeptide fragment thereof, is directly introduced into cells. In accordance with one embodiment nucleic acid sequences encoding one or more bacterial effector proteins, or fragments thereof, are introduced into mammalian cells via a delivery vehicle, optionally wherein the delivery vehicle is targeted to a pre-selected population of cells.

In one embodiment the encoded bacterial effector protein is a protein produced by bacteria of the genus *Legionella* and in one embodiment the effector protein is the *Legionella pneumophila* protein, LegC4. In accordance with one embodiment nucleic acid sequences encoding a polypeptide having at least 85%, 90%, 95% or 99% sequence identity to SEQ ID NO: 2, or a polypeptide having at least 85%, 90%, 95% or 99% sequence identity to a peptide fragment of SEQ ID NO: 2 are provided. In one embodiment the nucleic acid sequences encoding a LegC4 protein are operably linked to a heterologous promoter that is functional in mammalian cells. In one embodiment the promoter is an inducible promoter. In one embodiment an expression vector is provided that can be packaged in a delivery vehicle capable of delivering the expression vector into the interior of mammalian cells for transient expression or for incorporation into the genome of the cell. In one embodiment the expression vector comprises a heterologous promoter operably linked to a nucleic acid sequence encoding a polypeptide having at least 85%, 90%, 95% or 99% sequence identity to SEQ ID NO: 2, or a nucleic acid sequence encoding a polypeptide having at least 85%, 90%, 95% or 99% sequence identity to a peptide fragment of SEQ ID NO: 2, wherein the peptide fragment is a contiguous 10, 15, 20, 50, 100, 300, 500, 800 or 1000 amino acid fragment of SEQ ID NO: 2.

In one embodiment the bacterial effector compositions disclosed herein are introduced into mammalian cells of a subject to stimulate cytokine-mediated host defense mechanisms. In one embodiment a nucleic acid sequence encoding one or more polypeptides having at least 95% sequence identity to SEQ ID NO: 2, or a nucleic acid encoding a peptide fragment of SEQ ID NO: 2 is introduced into cells to increase the intracellular concentration of the encoded one or more polypeptides and stimulate cytokine-mediated host defense mechanisms. In one embodiment the introduced nucleic acid encodes at least a contiguous 10, 15, 20, 50, 100, 300, 500, 800 or 1000 amino acid fragment of SEQ ID NO: 2. In one embodiment the introduced nucleic acid has at least 85%, 90%, 95% or 99% sequence identity to SEQ ID NO: 1, or a fragment thereof.

In accordance with one embodiment one or more polypeptides having at least 85%, 90%, 95% or 99% sequence identity to SEQ ID NO: 2, or a polypeptide having at least 85%, 90%, 95% or 99% sequence identity to a peptide fragment of SEQ ID NO: 2, optionally wherein said fragment is at least 10, 15, 20, 50, 100, 300, 500, 800 or 1000 amino acids in length, are introduced into mammalian cells of a subject to stimulate cytokine-mediated host defense mechanisms. The polypeptides can be introduced into mammalian cells via controlled and/or targeted delivery mechanisms, including for example by liposome or other membrane bound vesicle, nanoparticle, or a cell-penetrating peptide (CPP) mediated delivery.

In accordance with the present disclosure, delivery of a bacterial effector protein such as LegC4 (delivered either by intracellularly-expression of a gene, or extracellularly-delivered protein) to mammalian cells of a potential host subject represents a novel therapeutic to strengthen the ability of the potential host to resist infection and/or interfere with pathogen replication or viability. The administered bacterial effector compositions can be used along or in conjunction with any standard anti-microbial treatment. Since this approach does not target essential processes in pathogens, like antibiotics, this has the potential to be a long-term antimicrobial agent that bacteria and other pathogens cannot evolve to overcome. A long-term therapeutic agent not susceptible to pathogen resistance has a significant economic benefit. Intracellular pathogenic infections are more challenging to treat and have higher rates of relapse, and therefore, a therapeutic that enhances the host's ability to clear intracellular pathogens will have a cost savings since repeat treatments will not be needed. Additionally, this approach will not contribute to the progression of antibacterial resistance when used as a therapeutic against bacterial pathogens, including but not limited to intracellular bacterial pathogens.

In accordance with one embodiment a method of treating or preventing an intracellular pathogen infection in a mammalian cell is provided, wherein the method comprises introducing a LegC4 polypeptide, or a fragment thereof, into the mammalian cell. In one embodiment the LegC4 polypeptide or a fragment thereof is introduced into the cell by transfecting the cell with a nucleic acid that encodes the LegC4 polypeptide or fragment thereof. In one embodiment the cell is transfected with a polynucleotide that encodes a polypeptide having at least 85%, 90%, 95% or 99% sequence identity to SEQ ID NO: 2, or a peptide fragment thereof that potentiate cytokine-mediated host defense mechanisms. In one embodiment the polynucleotide encoding the bacterial effector protein is operably linked to a non-native heterologous constitutive promoter that functions in mammalian cells, optionally wherein the promoter is a cytomegalovirus promoter.

In one embodiment the introduced nucleic acid sequence encoding the bacterial effector protein is transiently expressed in the mammalian cells. In one embodiment the expression of the bacterial effector protein (e.g., a LegC4 polypeptide) is under the control of an inducible promoter. In one embodiment the mammalian cells are stably transfected with the nucleic acid encoding the bacterial effector protein (e.g., the LegC4 polypeptide). In accordance with one embodiment the LegC4 encoding nucleic acid encodes a polypeptide of similar or identical size to SEQ ID NO: 2 and having at least 85%, 90%, 95% or 99% sequence identity to SEQ ID NO: 2, or a polypeptide having at least 85%, 90%, 95% or 99% sequence identity to a peptide fragment of SEQ ID NO: 2. In accordance with one embodiment the LegC4 encoding nucleic acid encodes a polypeptide of similar or identical size to SEQ ID NO: 2 and having at least 95% sequence identity to SEQ ID NO: 2, or a polypeptide having at least 95% sequence identity to a peptide fragment of SEQ ID NO: 2, optionally wherein the peptide fragment is a contiguous amino acid fragment of SEQ ID NO: 2 having a length of at least 10, 15, 20, 50, 100, 300, 500, 800 or 1000 amino acids. In one embodiment the LegC4 encoding nucleic acid encodes a polypeptide comprising the sequence of SEQ ID NO: 2.

In one embodiment the LegC4 polypeptide or a fragment thereof is introduced into the cell by transfecting the cell with a nucleic acid that encodes a peptide comprising at least a contiguous 10, 15, 20, 50, 100, 300, 500, 800 or 1000 amino acid fragment of SEQ ID NO: 2. In one embodiment the LegC4 polypeptide encoding nucleic acid is a nucleic acid encoding a polypeptide having at least 85%, 90%, 95% or 99% sequence identity to a peptide fragment of SEQ ID NO: 2. In one embodiment the LegC4 polypeptide encoding nucleic acid is a nucleic acid having at least 85%, 90%, 95% or 99% sequence identity to SEQ ID NO: 1. In one embodiment the LegC4 polypeptide encoding nucleic acid comprises the nucleic acid sequence of SEQ ID NO: 1.

In accordance with one embodiment a method of treating mammalian cells to inhibit the replication and/or reduce the numbers of an intracellular pathogen present in mammalian cells is provided, with the proviso that the intracellular bacterial pathogen is not *Legionella pneumophilia*. In one embodiment a method is provided for reducing the numbers of an intracellular pathogen present in mammalian cells contacted with said intracellular pathogen, relative to non-treated mammalian cells contacted with said intracellular pathogen, said method comprising increasing the intracellular concentration of a polypeptide having 95% sequence to SEQ ID NO: 2 (LegC4) in said treated cells, with the proviso that the intracellular bacterial pathogen is not *Legionella pneumophilia*. In one embodiment the mammalian cell is a human cell and more particularly the mammalian cell to be treated is in vivo.

In accordance with one embodiment a method of treating intracellular pathogens of mammalian cells is provided wherein the intracellular pathogen is a fungal, viral, or bacterial pathogen, wherein the bacterial pathogen is other than *Legionella pneumophilia*, said method comprising Introducing or increasing the concentration of a bacterial effector protein in a host cell. In one embodiment the viral pathogen treated in accordance with the present disclosure is a member of a viral family selected from the group consisting of Herpesviridae, Papillomaviridae, Coronaviridae, Flaviviridae, Filoviridae, Orthomyxoviridae and Retroviridae. In one embodiment the viral pathogen is a member of the Coronaviridae family, including but not limited to Human coronavirus 229E, Human coronavirus NL63, Human coronavirus OC43, Human coronavirus HKU1, Middle East respiratory syndrome-related coronavirus, Severe acute respiratory syndrome coronavirus, Severe acute respiratory syndrome coronavirus 2 (SARS-COV-2). In one embodiment a method of treating an intracellular bacterial infection is provided, wherein the bacterial pathogen is other than *Legionella pneumophilia*, said method comprising the step of introducing or increasing the concentration of a bacterial effector protein into host cell of an infected individual.

In one embodiment the intracellular bacterial pathogen treated in accordance with the present disclosure is selected from the group consisting of *Yersinia pestis, Burkholderia pseudomallei, Burkholderia mallei, Listeria monocytogenes, Pseudomonas aeruginosa, Brucella abortus, Chlamydia trachomatis, Coxiella burnetii, Mycobacterium tuberculosis, Salmonella enterica* and *Shigella flexneri* spp. In one embodiment the intracellular bacterial pathogen treated in accordance with the present disclosure is *Listeria monocytogenes, Pseudomonas aeruginosa* or *Salmonella enterica*.

In accordance with one embodiment a method of treating mammalian cells to inhibit the replication and/or reduce the numbers of an intracellular pathogen present in mammalian cells is provided, wherein said method comprises Introducing or increasing the concentration of a bacterial effector protein in the mammalian cells. In one embodiment the method of treating or preventing an intracellular pathogen infection in a mammalian cell comprises the step of increasing the intracellular concentration of a polypeptide having 95% sequence to SEQ ID NO: 2 (LegC4) in said cells, with the proviso that the intracellular bacterial pathogen is not *Legionella pneumophilia*. In one embodiment the intracellular concentration of a polypeptide having at least 95% sequence to SEQ ID NO: 2 is increased by transfecting said cells with a polynucleotide that encodes said polypeptide, wherein the polynucleotide is operably linked to regulatory elements that allow for the expression of the encoded polypeptide in mammalian cells, including human cells. In one embodiment the mammalian cells are transfected with a polynucleotide that encodes a polypeptide of SEQ ID NO: 2 or a fragment thereof. In one embodiment the mammalian cells are transfected with a nucleic acid coding sequence comprising SEQ ID NO: 1, wherein the coding sequence is operably linked to regulatory elements allowing the expression of the protein encoded by SEQ ID NO: 1.

EXEMPLIFIED EMBODIMENTS

In accordance with embodiment 1 a method of treating mammalian cells to prevent an intracellular pathogen infection, or suppress or reduce the numbers of an intracellular pathogen present in mammalian cells after an infection with said intracellular pathogen or reduce the total number of infected cells in subject, is provided wherein the intracellular concentration of a bacterial effector protein, optionally a polypeptide of similar size (e.g., being at least 90% or 95% the length of SEQ ID NO: 2) or identical in sized to SEQ ID NO: 2 and having at least 80%, 85%, 95% or 99% sequence identity to SEQ ID NO: 2 (LegC4), or a peptide fragment thereof having at least 95% sequence identity to a contiguous fragment of SEQ ID NO: 2, wherein said fragment is at least 10, 15, 20, 50, 100, 300, 500 or 1,000 amino acids in length is increased in said cells, with the proviso that the intracellular bacterial pathogen is not *Legionella pneumophilia*.

In accordance with embodiment 2, the method of embodiment 1 is provided wherein the step of increasing the intracellular concentration of said polypeptide comprises delivering an exogenous source of said polypeptide, or a polynucleotide encoding said polypeptide, into the interior of said mammalian cells.

In accordance with embodiment 3, the method of embodiment 1 or 2 is provided wherein the intracellular concentration of said polypeptide is increased by transfecting said cells with a polynucleotide that encodes said polypeptide, optionally wherein said polynucleotide encodes a polypeptide of similar size (e.g., being at least 90% or 95% the length of SEQ ID NO: 2) or identical size to SEQ ID NO: 2 and having at least 95% sequence identity to SEQ ID NO: 2, or a polypeptide fragment of SEQ ID NO: 2, wherein said fragment has at least 95% sequence identity to a contiguous 10, 15, 20, 50, 100, 300, 500 or 1,000 amino acid fragment of SEQ ID NO: 2.

In accordance with embodiment 4, the method of any one of embodiments 1-3 is provided wherein said cells are transfected with a polynucleotide that encodes said polypeptide, wherein said polynucleotide is operably linked to a non-native, heterologous regulatory element (promoter) allowing for expression of said polypeptide in a mammalian cell, optionally wherein said promoter is an inducible promoter.

In accordance with embodiment 5, the method of embodiment 4 is provided wherein the cells are transiently transfected with said polynucleotide, and said promoter is a constitutive promoter that functions in mammalian cells.

In accordance with embodiment 6, the method of any one of embodiments 1-5 is provided wherein the intracellular concentration of said polypeptide is increased in a targeted population of cells.

In accordance with embodiment 7, the method of any one of embodiments 1-6 is provided wherein said cells are transfected with a polynucleotide having at least 95% sequence to SEQ ID NO: 1, wherein the sequence of SEQ ID NO: 1 is operably linked to heterologous promoter that functions in mammalian cells.

In accordance with embodiment 8, the method of any one of embodiments 2-7 is provided wherein the cells are stably transfected with said polynucleotide, optionally wherein said polynucleotide is operably linked to an inducible promoter.

In accordance with embodiment 9, the method of any one of embodiments 1-8 is provided wherein the mammalian cell is a human cell.

In accordance with embodiment 10, the method of any one of embodiments 1-9 is provided wherein the intracellular pathogen is an intracellular bacterial pathogen.

In accordance with embodiment 11, the method of embodiment 10 is provided wherein the intracellular pathogen is selected from the group consisting of *Yersinia pestis, Burkholderia pseudomallei, Burkholderia mallei, Listeria monocytogenes, Pseudomonas aeruginosa, Brucella abortus, Chlamydia trachomatis, Coxiella burnetii, Mycobacterium tuberculosis, Salmonella enterica* and *Shigella flexneri* spp.

In accordance with embodiment 12, the method of embodiment 11 is provided wherein the intracellular pathogen is *Listeria monocytogenes, Pseudomonas aeruginosa* or *Salmonella enterica*.

In accordance with embodiment 13, the method of embodiment 11 is provided wherein the intracellular pathogen is *Listeria monocytogenes* or *Salmonella enterica.*

In accordance with embodiment 14, the method of any one of embodiments 1-9 is provided wherein the intracellular pathogen is a viral pathogen, optionally a viral pathogen selected from the viral family of Herpesviridae, Papillomaviridae, Coronaviridae, Flaviviridae, Filoviridae, Orthomyxoviridae or Retroviridae, optionally wherein the viral pathogen is a member of the Coronaviridae family.

In accordance with embodiment 15, the method of any one of embodiments 1-14 is provided wherein said mammalian cell is treated in vivo by administering to a subject a delivery vehicle that introduces a polynucleotide into the interior of mammalian cells, wherein said polynucleotide encodes a bacterial effector protein, optionally wherein said polynucleotide encodes a polypeptide of similar size (e.g., being at least 90% or 95% the length of SEQ ID NO: 2) or identical in size to SEQ ID NO: 2 and having at least 80%, 85% 95% or 95% sequence identity to SEQ ID NO: 2, or encodes a contiguous fragment of the polypeptide of SEQ ID NO: 2, wherein said fragment is at least 10, 15, 20, 30, 50, 100, 300, 500 or 1,000 amino acids in length, optionally wherein the mammalian cell is a human cell.

In accordance with embodiment 16, the method of any one of embodiments 1-14 is provided wherein, the mammalian cells are treated in vivo by administering to a subject a composition that introduces a bacterial effector protein into said cells, optionally wherein said bacterial effector protein comprises a polypeptide having at least 80%, 85%, 95% or 99% sequence identity to SEQ ID NO: 2, optionally wherein the mammalian cells are human cells.

In accordance with embodiment 17, the method of embodiment 15 is provided wherein said polynucleotide is introduced into the cell via a viral delivery vehicle.

In accordance with embodiment 18, the method of embodiment 16 is provided wherein a polypeptide having at least 80%, 85%, 95% or 99% sequence identity to SEQ ID NO: 2 is introduced into said cell via a delivery vehicle that delivers said polypeptide into the cytosol of said cell, optionally wherein the delivery vehicle is an extracellular vesicle.

In accordance with embodiment 19, the method of any one of embodiments 1-18 is provided further comprising the step of increasing the intracellular concentration of a second bacterial effector protein that is structurally distinct from the first bacterial effector protein.

In accordance with embodiment 20, a method of inhibiting an intracellular pathogen present in mammalian cells is provided, said method comprising the step of increasing the intracellular concentration of one or more bacterial effector proteins in said cells, optionally wherein said effector proteins comprise a polypeptide having at least 95% sequence identity to SEQ ID NO: 2 (LegC4), or a contiguous fragment thereof, wherein said fragment is at least 10, 15, 20, 30, 50, 100, 300, 500 or 1,000 amino acids in length, with the proviso that the intracellular bacterial pathogen is not *Legionella pneumophilia*, optionally wherein the mammalian cell is a human cell.

In accordance with embodiment 21, the method of embodiment 20 is provided wherein the step of increasing the intracellular concentration of said polypeptide comprises delivering an exogenous source of said polypeptide, or a polynucleotide encoding said polypeptide, into the interior of said mammalian cells.

In accordance with embodiment 22, the method of embodiment 20 or 21 is provided wherein the intracellular concentration of a polypeptide having at least 95% sequence identity to SEQ ID NO: 2 is increased by transfecting said cells with a polynucleotide that encodes said polypeptide.

In accordance with embodiment 23, the method of any one of embodiments 20-22 is provided wherein said cells are transfected with a polynucleotide encoding said polypeptide, wherein said polynucleotide is operably linked to regulatory element allowing for expression of said polypeptide in a mammalian cell, optionally wherein the regulatory element is a non-native heterologous promotor that is not operably linked to the polypeptide encoding sequence in nature.

In accordance with embodiment 24, the method of any one of embodiments 20-23 is provided wherein said cells are transfected with a polynucleotide having at least 95% sequence similarity to SEQ ID NO: 1.

In accordance with embodiment 25, the method of any one of embodiments 20-24 is provided wherein said polynucleotide is operably linked to an inducible promoter.

In accordance with embodiment 26, the method of any one of embodiments 20-25 is provided wherein the mammalian cell is a human cell.

In accordance with embodiment 27, the method of any one of embodiments 20-26 is provided wherein the intracellular pathogen is an intracellular bacterial pathogen, with the proviso that the bacterial pathogen is not *Legionella pneumophilia.*

In accordance with embodiment 28, the method of embodiment 27 is provided wherein the intracellular pathogen is selected from the group consisting of *Yersinia pestis, Burkholderia pseudomallei, Burkholderia mallei, Listeria monocytogenes, Pseudomonas aeruginosa, Brucella abortus, Chlamydia trachomatis, Coxiella burnetii, Mycobacterium tuberculosis, Salmonella enterica* and *Shigella flexneri* spp.

In accordance with embodiment 29, the method of embodiment 28 is provided wherein the intracellular pathogen is *Listeria monocytogenes, Pseudomonas aeruginosa* or *Salmonella enterica.*

In accordance with embodiment 30, the method of embodiment 28 is provided wherein the intracellular pathogen is *Listeria monocytogenes* or *Salmonella enterica.*

In accordance with embodiment 31, the method of any one of embodiments 20-26 is provided wherein the intracellular pathogen is a viral pathogen, optionally a viral pathogen selected from the viral family of Herpesviridae, Papillomaviridae, Coronaviridae, Flaviviridae, Filoviridae, Orthomyxoviridae or Retroviridae, optionally wherein the viral pathogen is a member of the Coronaviridae family.

In accordance with embodiment 32, the method of any one of embodiments 20-31 is provided wherein said mammalian cell is treated in vivo by administering to a subject a delivery vehicle that introduces a polynucleotide that encodes a polypeptide having at least 80%, 85% 95% or 95% sequence identity to SEQ ID NO: 2, or a peptide fragment of SEQ ID NO: 2, into the interior of said mammalian cell, optionally wherein the mammalian cell is a human cell.

In accordance with embodiment 33, the method of any one of embodiments 20-31 is provided wherein said mammalian cell is treated in vivo by administering a composition that introduces a polypeptide having at least 80%, 85%, 95% or 99% sequence identity to SEQ ID NO: 2, or a peptide fragment of SEQ ID NO: 2, said fragment being at least 10, 15, 20, 30, 50, 100, 300, 550 or 1,000 amino acids in length, into said mammalian cell, optionally wherein the mammalian cell is a human cell.

In accordance with embodiment 34, the method of any one of embodiments 20-33 is provided wherein a polypeptide having at least 80%, 85%, 95% or 99% sequence identity to SEQ ID NO: 2, or peptide fragment of SEQ ID NO: 2, said fragment being at least 10, 15, 20, 30, 50, 100, 300, 550 or 1,000 amino acids in length, is introduced into said cell by transfecting the cell with a polynucleotide that encodes said polypeptide, and expressing said polypeptide in said cell, optionally wherein the mammalian cell is a human cell.

In accordance with embodiment 35, the method of embodiment 34 is provided wherein the polynucleotide is introduced into the cell via a viral delivery vehicle.

In accordance with embodiment 36, the method of embodiment 33 is provided wherein said polypeptide is introduced into the cytosol of said cell via a delivery vehicle, optionally wherein the delivery vehicle is an extracellular vesicle.

In accordance with embodiment 37 the method of any one of embodiments 1-35 is provided wherein the intracellular concentration of a polypeptide having at least 95% sequence to SEQ ID NO: 2 is increased by transfecting said cell with a polynucleotide that encodes said polypeptide, optionally wherein the polynucleotide has at least 95% sequence identity to SEQ ID NO: 1.

In accordance with embodiment 38 a pharmaceutical composition is provided comprising a delivery vehicle and a pharmaceutically acceptable excipient, wherein said delivery vehicle is capable of delivering its contents to the interior of mammalian cells and comprises:

i) a polypeptide of similar size (e.g., being at least 90% or 95% the length of SEQ ID NO: 2) or identical in sized to SEQ ID NO: 2 and having at least 80%, 85%, 95% or 99% sequence identity to SEQ ID NO: 2 (LegC4), or a peptide fragment thereof having at least 95% sequence identity to a contiguous fragment of SEQ ID NO: 2, wherein said fragment is at least 10, 15, 20, 50, 100, 300, 500 or 1,000 amino acids in length, or ii) a polynucleotide encoding a polypeptide of similar size (e.g., being at least 90% or 95% the length of SEQ ID NO: 2) or identical in sized to SEQ ID NO: 2 and having at least 80%, 85%, 95% or 99% sequence identity to SEQ ID NO: 2 (LegC4), or a peptide fragment thereof having at least 95% sequence identity to a contiguous fragment of SEQ ID NO: 2, wherein said fragment is at least 10, 15, 20, 50, 100, 300, 500 or 1,000 amino acids in length.

In accordance with embodiment 39, the composition of embodiment 38 is provided wherein said delivery vehicle comprises a polynucleotide encoding a polypeptide having at least 95% sequence identity with the polypeptide of SEQ ID NO: 2.

In accordance with embodiment 40, the composition of embodiment 38 is provided wherein said delivery vehicle comprises a polypeptide having at least 95% sequence identity with the polypeptide of SEQ ID NO: 2.

In accordance with embodiment 41, the composition of embodiment 38 or 39 is provided wherein said delivery is a viral delivery vehicle.

In accordance with embodiment 42, the composition of embodiment 38 or 40 is provided wherein said delivery is an extracellular vesicle.

In accordance with embodiment 43, the composition of any one of embodiments 38-42 is provided further comprising an antimicrobial agent, optionally wherein the antimicrobial agent is an antibiotic.

In accordance with embodiment 44, a viral vector is provided wherein said vector is capable of delivering its contents to the interior of a mammalian cell and further comprises a polynucleotide that encodes a polypeptide having at least 95% sequence identity to SEQ ID NO: 2, or encodes a contiguous peptide fragment of SEQ ID NO: 2, wherein the fragment is at least 10, 15, 20, 30, 50, 100, 300, 500 or 1,000 amino acids in length, further wherein said polynucleotide is operably linked to a heterologous promoter capable of expressing said polypeptide in a mammalian cell.

In accordance with embodiment 45, the viral vector of embodiment 44 is provided wherein the viral vector is derived from a retrovirus, adenovirus, adeno-associated virus, lentivirus or herpes simplex virus, optionally wherein the viral vector is an adenovirus, adeno-associated virus derived vector.

In accordance with embodiment 46, the viral vector of embodiment 44 or 45 is provided wherein said promoter is an inducible promoter.

In accordance with embodiment 47, a recombinant polynucleotide is provided wherein said polynucleotide encodes i) a polypeptide of similar size (e.g., being at least 90% or 95% the length of SEQ ID NO: 2) or identical size to SEQ ID NO: 2, and having at least 95% sequence identity to SEQ ID NO: 2, or ii) a polypeptide fragment of SEQ ID NO: 2, wherein said fragment has at least 95% sequence identity to a contiguous 10, 15, 20, 50, 100, 300, 500 or 1,000 amino acid fragment of SEQ ID NO: 2, wherein said polynucleotide is operably linked to a promoter capable of expressing said polypeptide in a mammalian cell, optionally wherein said promoter is an inducible promoter.

In accordance with embodiment 48, any of the methods or compositions of embodiments 1-47 is provided wherein a cytomegalovirus promoter is operably linked to a polynucleotide that encodes a bacterial effector protein, optionally wherein the encoded protein comprises a polypeptide having at least 95% sequence identity with SEQ ID NO: 2 or a fragment thereof.

EXAMPLES

Example 1: Antibacterial Activity of LegC4 in Reducing Intracellular Bacterial Populations To evaluate the antibacterial efficacy of LegC4 expressed in host cells against intracellular pathogens, LegC4 is delivered to host cells that are then challenged by contact with intracellular bacterial populations.

Methods

HeLa (ATCC CCL2) cells were cultured in Dulbecco's Modified Eagle's Medium (DMEM) supplemented with 10% Fetal Bovine Serum (FBS) and 1% Penicillin-Streptomycin at 37° C., 5% $CO_2$. Cells were seeded in 24-well cell culture plates 24-48 hours prior to the start of transfection (until 70-80% confluency per well was reached). Plasmids expressing LegC4 with or without a Green Fluorescent Protein (GFP) tag (legC4_pCMV6-AN-GFP; legC4_pCMV6) were purchased from Blue Heron Bio and purified in-house by Midi-Prep (Qiagen Midi-Prep kit, Qiagen) from *Escherichia coli* bacterial stabs.

Cells were transfected with Lipofectamine 3000 according to manufacturer's instructions (Thermo Fisher Scientific) at a concentration of 500 ng DNA per well. 48 hours post-transfection, cells were washed twice with Dulbecco's phosphate-buffered saline (DPBS) and media was replaced with DMEM, 10% FBS, without antibiotic. In each 24-well plate, triplicate wells were either left untransfected or transfected with LegC4-GFP or LegC4 alone. GFP expression was imaged on a Zeiss Axiovert Microscope.

*Shigella flexneri* spp. Castellani and Chalmers (ATCC 700930) and *Salmonella enterica* serovar *typhimurium* (ATCC 14208) were incubated on Tryptic Soy Agar (TSA) plates at 37° C. overnight. Both bacterial strains were cultured overnight in Tryptic Soy Broth (TSB) at 37° C. The day of infection (48-hours post-transfection of cells), bacteria were subcultured into TSB and grown to an absorbance (A600) of ~1.00 (exact values: *S. flexneri*, 1.301; *S. enterica*, 1.054) in shaking flasks, 37° C.

Bacterial suspensions were prepared in DMEM (10% FBS, no antibiotic) to provide a multiplicity of infection (MOI) of 10 when 0.35 mL of the suspension was added to each well of a 24 well plate. Spent media was removed from the cells prior to adding the bacterial suspension. After inoculation, cells were incubated for 1 hour at 37° C., 5% $CO_2$. After 1 hour, supernatant was removed from each well and cells were washed twice with Phosphate Buffered Saline (PBS) to remove uninvaded bacteria. Extracellular bacteria were killed by the addition of 50 µg/ml Gentamicin (in cell culture media) for 30 minutes at 37° C., 5% $CO_2$. Cells were then washed twice and fresh media containing 5 µg/mL gentamicin was added.

At each time point (1-, 3-, 24-, or 48-hour post-infection), supernatants were collected, and cells were washed twice and lysed in 0.35 mL 1% Triton X-100 for 15 minutes at room temperature. Lysates were collected by scraping wells with a pipette tip and pipetting. Cell lysates were kept on wet-ice while processing.

Lysates were serially diluted 10-fold in PBS and 0.1 mL was plated onto TSA plates in triplicate and incubated overnight at 37° C. Note, bacterial inoculation suspensions were also serially diluted 10-fold and plated on TSA for quantification of inoculum.

Bacteria were quantified by counting and recording colony forming units (CFUs) in a countable range of 30-300 colonies per plate. $Log_{10}$ reduction in intracellular bacteria in each sample was determined by subtracting the average $log_{10}$ recovered from transfected wells from the $log_{10}$ CFU recovered from untransfected samples. Statistical analysis was performed in GraphPad Prism. Supernatant and lysate samples were all stored at −80° C. for future analysis.

Results

Transfection and Expression of LegC4 in Hela Cells

Efficiency of transfection was assessed by fluorescence microscopy. Expression of LegC4-AN-GFP was detected by signal in the FITC channel due to expression of GFP. GFP expression was not detected above background levels in cells that were transfected with LegC4 alone (no GFP reporter tag). Images were taken on the day of infection (48-hours post-transfection).

Expression of LegC4 Controls Intracellular Infection of *Salmonella*

Because *Shigella* did not survive in untransfected or transfected Hela cells past 3 hours (within this experiment), no further analysis was performed on *Shigella*. *Salmonella* survived in all three cellular conditions out to 48-hours post-infection. However, expression of either LegC4-GFP or LegC4 alone resulted in a near-significant (LegC4-GFP, p value=0.053; LegC4 alone, p value=0.053) reduction of intracellular *S. enterica* compared to untransfected cells (FIG. 1A).

Figure 1B:
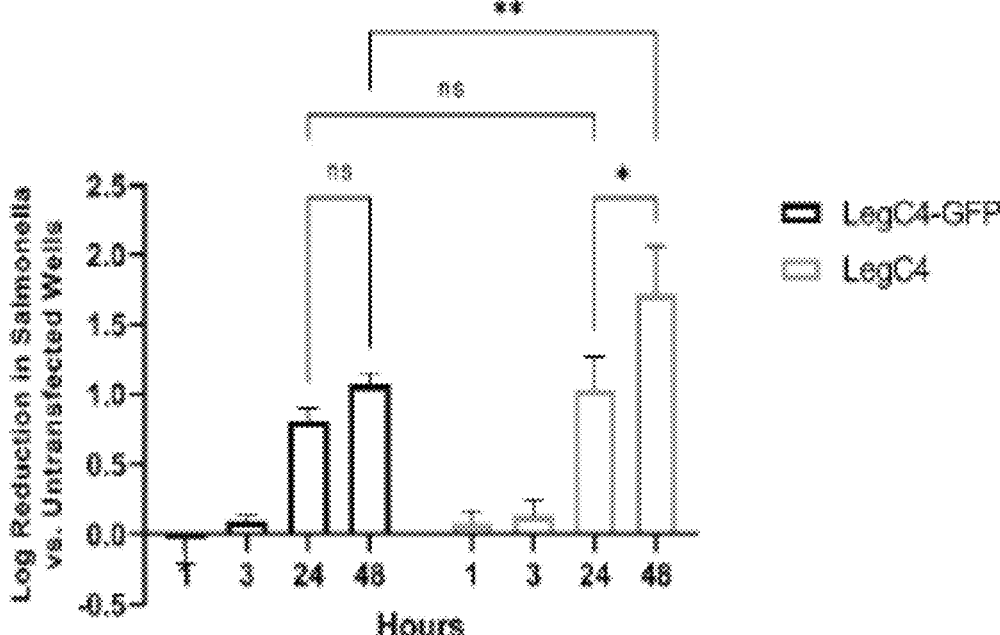

When the data is analyzed as log reduction in *S. enterica* versus untransfected cells (FIG. 1B), a clear trend of increasing antibacterial effect (log reduction) is observed over time. Of note, a significant increase (p=0.0076) was observed between the log reduction in *S. enterica* at 48 hours in cells expressing LegC4 alone compared to LegC4-GFP, suggesting that the presence of the GFP reporter tag may have an inhibitory effect on the activity of the LegC4 protein.

Finally, in cells transfected with LegC4 alone, a significant increase in log reduction was observed between 24 and 48-hours post-transfection (p=0.0107), suggesting that the activity of LegC4, as an immune effector, may have the greatest effect at reducing or preventing survival of intracellular bacteria rather than preventing entry of bacteria into the cell in early stages of infection.

Example 2: Antibacterial and Antiviral Activity of LegC4-expressing Mammalian Cells Methods Intracellular Bacterial Survival Assay Overview Hela cells were left untransfected or were transfected with plasmids expressing LegC4 with or without a Green Fluorescent Protein (GFP) tag (legC4_pCMV6-AN-GFP; legC4_pCMV6). GFP expression was imaged. Cells were then infected with *Listeria monocytogenes* and *Pseudomonas aeruginosa*. At each time point, supernatants and lysates were collected. Lysates were serially diluted, plated, and incubated overnight consistent with the procedures detailed in Example 1.

Viral Survival Assay Overview

MRC-5 cells were left untransfected or were transfected with plasmids expressing LegC4 with or without a GFP tag (legC4_pCMV6-AN-GFP; legC4_pCMV6). Cells were then infected with HCoV-OC43, a human coronavirus surrogate. At each time point, supernatants were collected and stored. Cytopathic effects (CPE) were read after a 4-day incubation period. After the last time point, a viral TCID-50 assay was performed to quantify viral titer.

Results

Transfection and Expression of LegC4 in Hela Cells

Efficiency of transfection was assessed by fluorescence microscopy. Expression of LegC4-AN-GFP was detected by signal due to expression of GFP. GFP expression was not detected above background levels in cells that were transfected with LegC4 alone.

*Pseudomonas aeruginosa*

Figures 2, 3:
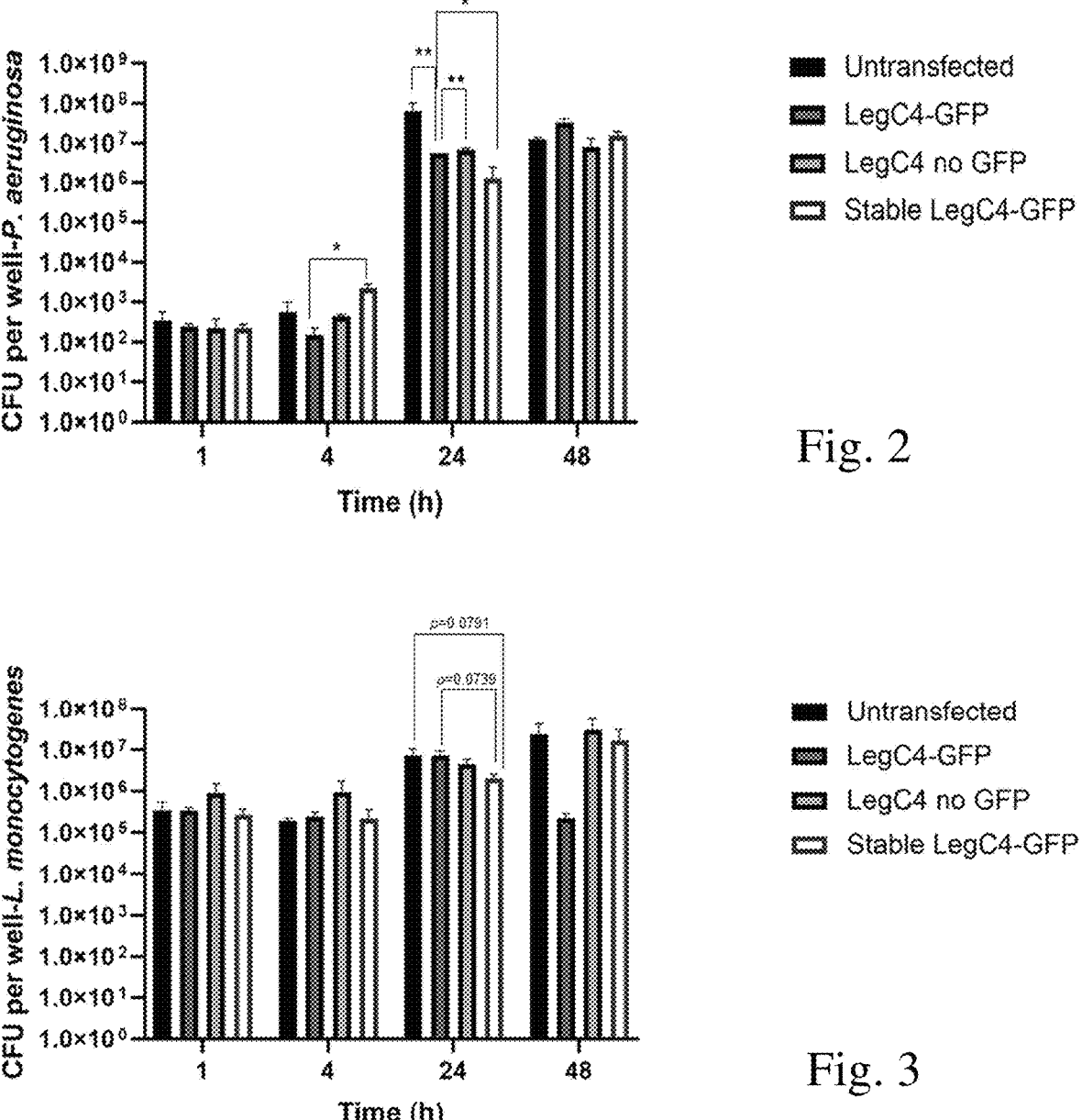
FIG. 2: is a bar graph showing the intracellular survival of *Pseudomonas* in LegC4 transfected cells. **, $p<0.005$, *, $p<0.05$ by ANOVA.
FIG. 3. is a bar graph showing the intracellular survival of *Listeria* in LegC4 transfected cells.

A significant reduction of *P. aeruginosa* was seen between untransfected cells and cells expressing Leg-GFP at 24 hours post infection (see FIG. 2).

*Listeria monocytogenes*

A near-significant reduction (p value=0.0791) of *L. monocytogenes* was seen at the 24-hour time point between the untransfected cells and the cells with stable LegC4 expression (see FIG. 3).

Expression of LegC4 Controls Viral Infection of HCoV-OC43

Figures 4, 5:
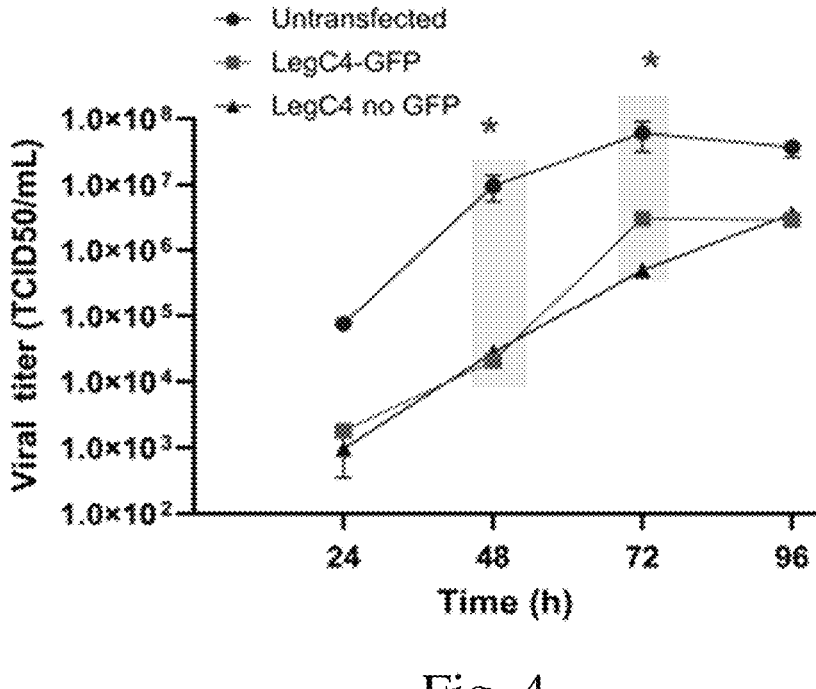
FIG. 4. is a graph showing the survival of HCoV-OC43 in LegC4 transfected MRC-5 cells.
FIG. 5. provides images of the cytopathic effects (CPE) of LegC4 transfected vs. non-transfected cells infected with HCoV-OC43).

A significant reduction of HCoV-OC43 was seen in cells expressing LegC4 at both the 48- and 72-hour time point post infection (FIG. 4). Of note, a 1000-fold decrease in viral titer was identified at 48 hours. CPE observation depicted that the untransfected cells began to show morphological changes beginning at 48 hours post infection. In the LegC4 conditions, CPE was not observed until the 96-hour time point, suggesting that the presence of LegC4 may delay the onset of infection (FIG. 5).

The invention claimed is:

1. A method of treating mammalian cells to suppress the numbers of an intracellular pathogen present in mammalian cells contacted with said intracellular pathogen, relative to non-treated mammalian cells contacted with said intracellular pathogen, said method comprising increasing the intracellular concentration in said mammalian cells, of a polypeptide having at least 95% sequence identity to SEQ ID NO: 2, or having at least 95% sequence identity to a peptide fragment of SEQ ID NO: 2, wherein said fragment is at least 20 amino acids in length via administering the polypeptide or a polynucleotide encoding said polypeptide to the mammalian cells, with the proviso that the intracellular pathogen is not *Legionella pneumophilia*.

2. The method of claim 1 wherein the step of increasing the intracellular concentration of said polypeptide comprises delivering an exogenous source of said polypeptide, or a polynucleotide encoding said polypeptide, into said mammalian cells.

3. The method of claim 1 wherein the intracellular concentration of said polypeptide is increased by transfecting said cells with a polynucleotide that encodes a polypeptide having at least 95% sequence identity to SEQ ID NO: 2.

4. The method of claim 3 wherein said cells are transfected with a polynucleotide having at least 95% sequence identity to SEQ ID NO: 1.

5. The method of claim 1 wherein the mammalian cell is a human cell.

6. The method of claim 1 wherein the intracellular pathogen is an intracellular bacterial pathogen selected from the group consisting of *Brucella abortus, Listeria monocytogenes, Chlamydia trachomatis, Coxiella burnetii, Mycobacterium tuberculosis, Salmonella enterica, Pseudomonas aeruginosa, Yersinia pestis, Burkholderia pseudomallei* and *Burkholderia mallei.*

7. The method of claim 1 wherein the intracellular pathogen is *Listeria monocytogenes, Pseudomonas aeruginosa* or *Salmonella enterica.*

8. The method of claim 1 wherein the intracellular pathogen is a viral pathogen.

9. The method of claim 1 wherein said cell is treated in vivo and the method comprises administering to a subject a composition comprising a delivery vehicle that delivers said polypeptide and/or said polynucleotide into the cytosol of the subject's cells.

10. The method of claim 9 wherein the delivery vehicle is an extracellular vesicle.

11. The method of claim 9 wherein the delivery vehicle is a viral vector.

12. A method of inhibiting the infection of a human cell by an intracellular pathogen, said method comprising the step of increasing the intracellular concentration in said human cell, of a polypeptide having at least 95% sequence identity to SEQ ID NO: 2 (LegC4), or having at least 95% sequence identity to a peptide fragment of SEQ ID NO: 2, wherein said fragment is at least 20 amino acids in length via administering the polypeptide or a polynucleotide encoding said polypeptide to the human cell, with the proviso that the intracellular pathogen is not *Legionella pneumophilia.*

13. The method of claim 12 wherein the intracellular pathogen is a bacterial intracellular pathogen selected from the group consisting of *Brucella abortus, Listeria monocytogenes, Chlamydia trachomatis, Coxiella burnetii, Mycobacterium tuberculosis, Salmonella enterica, Pseudomonas aeruginosa, Yersinia pestis, Burkholderia pseudomallei* and *Burkholderia mallei.*

14. The method of claim 13 wherein the intracellular pathogen is *Listeria monocytogenes, Pseudomonas aeruginosa* or *Salmonella enterica.*

15. The method of claim 12 wherein the intracellular pathogen is a viral pathogen.

16. The method of claim 13 wherein the intracellular concentration of a polypeptide having at least 95% sequence identity to SEQ ID NO: 2 is increased by transfecting said cell with a polynucleotide that encodes said polypeptide.

17. The method of claim 16 wherein the cell is transfected with a polynucleotide having at least 95% sequence identity to SEQ ID NO: 1.

18. A method of treating mammalian cells to suppress the numbers of an intracellular viral pathogen present in mammalian cells contacted with said intracellular viral pathogen, relative to non-treated mammalian cells contacted with said intracellular viral pathogen, said method comprising transfecting the cells with a nucleic acid that encodes for a polypeptide having at least 95% sequence identity to SEQ ID NO: 2 or a peptide fragment of SEQ ID NO: 2, wherein said peptide fragment is at least 20 amino acids in length.

19. The method of claim 18, wherein the cells are human cells that are transfected with a polynucleotide having at least 95% sequence identity to SEQ ID NO: 1.

* * * * *

SEQUENCE LISTING

```
Sequence total quantity: 2
SEQ ID NO: 1           moltype = DNA   length = 2283
FEATURE                Location/Qualifiers
source                 1..2283
                       mol_type = genomic DNA
                       organism = Legionella pneumophila
SEQUENCE: 1
ttgattcatt atgtatcctt gattcatttc aatgagctgt ttgagattat gaaacccaat   60
ttgtttact  ttgtattgac gcatatttta gctgaatccc caaatcttaa attattagat  120
gagattacac cggtccatga tattacctta aaagataaga agtattatcg cttagaatta  180
ccccttggcta atattgctgc agaaggattc aggctgcatg acgcgcatat tagtctttat  240
gagaagacag atccccataa tccaaattta ggactttcgc attttactgc gatcttccat  300
gatcaaaatg gtcaaaccta tcgaatgcat ttgtttttga atcgtttcga cgctctggca  360
tgcccagcta cctgggagtt attggatgat gatgagcaat atgtcaaagt tcccccacca  420
gaaaatctgg aatatttcat tcattctgta tggcagctag gcctgccttg tttgcaattg  480
ttgcgaaaaa agcaaaagga aatagaagct aaattgcttg ctgattacca cagattaaac  540
gaggaaacga cttcactaag taaggattta gataaaaaca gagcggtcta tttgaaaaag  600
cttgatgaat taattaagac gactaaatca ttaagccaaa tttctgaaag taatcattgg  660
ttgagagaag caatttacct gggggaaaaca cacaagtacg tatcctctat gccggaacca  720
attcttgagc ctgttaaaaa aagtgatgaa gagcataaaa aagatgacaa agcagaggtt  780
gttgccttgt ctccaaagca aggggctacg gagcccaaaa tcagcagagg caatatcggg  840
ctttctcaat cgaccttatt ttccaaatca gccaaagcga aacgccctgt ggatgtgaaa  900
atggagcgcg atattagcaa gataaaaaaa ttgtttgctc aactattaaa gacggaagat  960
aaaaaaatta aagcagttct tttaattgat ttacattgga aaatcaaaga aataaatttg 1020
gaaacggaag agttactgac aaaagagcaa acacaagccc taaatgaaat cgaaggccgt 1080
gcaaataaag aagccaagtc actcctggaa agagctttgt ttgctggaga gtttgaatac 1140
gctcaaaccc tgtcgcctta ttatcctttg attaataatg atctaatggt tcttgcgctt 1200
actcagagaa aagctgatct tttaagcttt ttagtcacta aagttggttt gcctatcaat 1260
agttatccaa ttaaaacaaa agcgcaaacg tattccaatg ccgttgagta ttgcttctca 1320
gaacatagtg aatcgttggt agactgcttt agcgtgttaa taaaaaatgg cgcaagtttg 1380
atgcagcctg ttggcttaca taaattacct ttagcccatc ttcttttgtc tgaaatcccc 1440
aggcacccct tgcacgccgc gttagaacaa aacaaaaatt tacctctcaa taacaagcaa 1500
ttttatgctc atttaattaa tgcactaaaa tcatgtttat tatctggtga tatcgaaggt 1560
gaccagaaaa ttgccctgga agagtccatt gtgcgatacg agcacttaaa gattaatgta 1620
aaaaactcat cctcactttt gagtcctcaa aaccaggcat tggctgatga aataagcgat 1680
attaccaaaa aattattgcc tgacgctgtg gctgaagcaa ttgagaatga tgaggaaata 1740
tcaagagaaa aagcaatcgc tgataaagaa tataaagaat tgattcgtaa ggtgaaggca 1800
ttttatcata aaaccggaaa gaactttgct tttcaatcct taattaattc agccaatcag 1860
gaattgaaga aagaattatt agaaattgac tttaatatcg acattagctt tagcgagctt 1920
aaggaatcca tactggaaaa cttaagcaag gaaagattaa tgttcagcta ttgcagtgaa 1980
ttaatagacg ttcaaagaac aatcatgcaa atatcgcagg gagcgagcag aaagaataaa 2040
aacctgaaaa aactcaatgc gcgacatgct gagcttatcg aattgctcac agatttaagc 2100
caaaatacgc ctcaatctat gataaaagaa gccaatgaat tcaagattc ttttagtcag 2160
cttcaagatt tattgaatgg cttgaatcaa ttggagggct cttttggcat gcttgctgga 2220
gtattaaatc aattccttga gggctcaaca tcggaatcag aatcttttga tattaagcta 2280
taa                                                                2283

SEQ ID NO: 2           moltype = AA   length = 760
FEATURE                Location/Qualifiers
source                 1..760
                       mol_type = protein
                       organism = Legionella pneumophila
SEQUENCE: 2
MIHYVSLIHF NELFEIMKPN LFYFVLTHIL AESPNLKLLD EITPVHDITL KDKKYYRLEL   60
PLANIAAEGF RLHDAHISLY EKTDPHNPNL GLSHFTAIFH DQNGQTYRMH LFLNRFDALA  120
CPATWELLDD DEQYVKVPPP ENLEYFIHSV WQLGLPCLQL LRKKQKEIEA KLLADYHRLN  180
EETTSLSKDL DKNRAVYLEK LDELIKTTKS LSQLSESNHW LREAIYLGKT HKYVSSMPEP  240
ILEPVKKSDE EHKKDDKAEV VALSPKQGAT EPKISRGNIG LSQSTLFSKS AKAKRPVDVK  300
MERDISKIKK LFAQLLKTED KKIKAVLLID LHWKIKEINL ETEELLTKEQ TQALNEIEGR  360
ANKEAKSLLE RALFAGEFEY AQTLSPYYPL INNDLMVLAL TQRKADLLSF LVTKVGLPIN  420
SYPIKTKAQT YSNAVEYCFS EHSESLVDCF SVLIKNGASL MQPVGLHKLP LAHLLLSEIP  480
RHPLHAALEQ NKNLTLNNKQ FYAHLINALK SCLLSGDIEG DQKIALEESI VRYEHLKINV  540
KNSSSLLSPQ NQALADEISD ITKKLLPDAV AEAIENDEEI SREKAIADKE YKELIRKVKA  600
FYHKTGKNFA FQSLINSANQ ELKKELLEID FNIDISFSEL KESILENLSK ERLMFSYCSE  660
LIDVQRTIMQ ISQGASRKNK NLKKLNARHA ELIELLTDLS QNTPQSMIKE ANEFQDSFSQ  720
LQDLLNGLNQ LEGSFGMLAG VLNQFLEGST SESESFDIKL                        760
```